(12) United States Patent
Spyrou et al.

(10) Patent No.: US 10,351,579 B2
(45) Date of Patent: Jul. 16, 2019

(54) MONOALLOPHANATES BASED ON ALKOXYSILANE ALKYL ISOCYANATES

(71) Applicant: EVONIK DEGUSSA GMBH, Essen (DE)

(72) Inventors: Emmanouil Spyrou, Schermbeck (DE); Manfred Kreczinski, Herne (DE); Tobias Unkelhaeusser, Duelmen (DE); Sabine Naumann, Herne (DE); Holger Loesch, Herne (DE); Marion Ewald, Marl (DE); Thomas Weihrauch, Duelmen (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 15/771,227

(22) PCT Filed: Oct. 11, 2016

(86) PCT No.: PCT/EP2016/074267
§ 371 (c)(1),
(2) Date: Apr. 26, 2018

(87) PCT Pub. No.: WO2017/071941
PCT Pub. Date: May 4, 2017

(65) Prior Publication Data
US 2018/0327432 A1    Nov. 15, 2018

(30) Foreign Application Priority Data

Oct. 29, 2015   (EP) .................................. 15192085

(51) Int. Cl.
| | | |
|---|---|---|
| C07F 7/18 | (2006.01) | |
| C08F 20/00 | (2006.01) | |
| C08G 18/62 | (2006.01) | |
| C08G 18/71 | (2006.01) | |
| C08G 18/78 | (2006.01) | |
| C09D 175/04 | (2006.01) | |
| C09D 133/06 | (2006.01) | |
| C07C 271/66 | (2006.01) | |
| C09J 175/04 | (2006.01) | |

(52) U.S. Cl.
CPC .......... *C07F 7/1804* (2013.01); *C07C 271/66* (2013.01); *C08F 20/00* (2013.01); *C08G 18/6225* (2013.01); *C08G 18/718* (2013.01); *C08G 18/7837* (2013.01); *C09D 133/066* (2013.01); *C09D 175/04* (2013.01); *C09J 175/04* (2013.01)

(58) Field of Classification Search
None
See application file for complete search history.

(56) References Cited

U.S. PATENT DOCUMENTS

| | | |
|---|---|---|
| 2007/0055010 A1 | 3/2007 | Ludewig et al. |
| 2007/0055035 A1 | 3/2007 | Ludewig et al. |
| 2008/0255354 A1* | 10/2008 | Popp ............... C07F 7/1892 544/221 |
| 2010/0010113 A1 | 1/2010 | Schwalm et al. |
| 2010/0098950 A1 | 4/2010 | Gruber et al. |
| 2014/0097392 A1 | 4/2014 | Berge et al. |
| 2016/0194341 A1 | 7/2016 | Haaf-Kleinhubbert et al. |
| 2017/0369626 A1 | 12/2017 | Stache et al. |
| 2017/0369627 A1 | 12/2017 | Stache et al. |
| 2017/0369631 A1 | 12/2017 | Stache et al. |
| 2017/0369736 A1 | 12/2017 | Stache et al. |

FOREIGN PATENT DOCUMENTS

| | | |
|---|---|---|
| DE | 10 2005 009 790 | 9/2006 |
| DE | 10 2005 041 953 | 3/2007 |
| DE | 10 2005 041 954 | 3/2007 |
| JP | 2015-101716 | 6/2015 |
| JP | 2015101716 A * | 6/2015 |
| WO | 2008/043722 | 4/2008 |
| WO | 2008/043723 | 4/2008 |
| WO | 2015/007588 | 1/2015 |

OTHER PUBLICATIONS

JP 2015101716 A (Jun. 4, 2015); Machine Translation. (Year: 2015).*
Ogasawara JP-2015101716-A—Machine Translation (Year: 2015).*
(Continued)

*Primary Examiner* — Clinton A Brooks
*Assistant Examiner* — Kofi Adzamli
(74) *Attorney, Agent, or Firm* — Grüneberg and Myers PLLC

(57) ABSTRACT

A monoallophanate can be used in paint or adhesive compositions. The monoallophanate has the formula 1:

$$R_n(R^1O)_{3-n}Si-R^2-N(C(O)OR^3)-C(O)-NH-R^4-Si(R^5O)_{3-m}R^6_m \quad (1)$$

where R, $R^1$-$R^6$ are each independently identical or different hydrocarbyl radicals having 1-8 carbon atoms, which may be branched or cyclic, or else may be integrated together to form a cyclic system, and m and n are each independently 0-2.

15 Claims, No Drawings

(56) References Cited

OTHER PUBLICATIONS

Ogasawara et al., "Organosiloxane compounds with excellent storage stability," Chemical Abstracts Services, Columbus, OH, Apr. 6, 2015, pp. 1-2.
International Search Report mailed in PCT/EP2016/074267 dated Jan. 2, 2017, with English translation.
Written Opinion of the International Searching Authority mailed in PCT/EP2016/074267 dated Jan. 2, 2017.
U.S. Appl. No. 15/770,733, filed Apr. 24, 2018, Emmanouil Spyrou.
U.S. Appl. No. 15/622,159, filed Jun. 14, 2017, 2017/0369626, Wiebke Stache.
U.S. Appl. No. 15/622,204, filed Jun. 14, 2017, 2017/0369736, Wiebke Stache.
U.S. Appl. No. 15/619,897, filed Jun. 12, 2017, 2017/0369627, Wiebke Stache.
U.S. Appl. No. 15/614,763, filed Jun. 6, 2017, 2017/0369631, Wiebke Stache.
Kozakiewicz et al., "New family of functionalized crosslinkers for heat-curable polyurethane systems—A preliminary study," Progress in Organic Coatings, Elsevier, vol. 72, 2011, pp. 120-130.

\* cited by examiner

MONOALLOPHANATES BASED ON ALKOXYSILANE ALKYL ISOCYANATES

This application is a National Stage entry under § 371 of International Application No. PCT/EP2016/074267, filed on Oct. 11, 2016, and claims priority to European Patent Application No. 15192085.7, filed on Oct. 29, 2015.

The invention relates to novel monoallophanates based on alkoxysilane alkyl isocyanates, to a process for preparation and to use.

Polyurethanes have been established for many decades as high-value components for paint, adhesive, sealant and plastics systems. It is possible here for additional alkoxysilane groups to play an important role, for example with regard to network density, chemical resistance and scratch resistance, primarily through the formation of siloxane structures. Systems of this kind are also known.

Molecules both possessing alkoxysilane groups and having isocyanate groups offer the option of introducing both the functionalities mentioned, siloxanes and polyurethane groups, by means of one component. Such substances too have long been in use, for example isocyanatoalkyltrialkoxysilanes. It is possible to use these substances, by reaction with polyalcohols, to prepare isocyanate-free moisture-curing crosslinkers.

In principle, such "SiPURs" (alkoxysilane-containing polyurethanes) can be reacted with further isocyanates to give allophanates, in order to modify particular material properties, for example viscosity.

For instance, DE102005041953A1 describes a reaction of a polyol having a mean molecular weight of 3000-20 000 g/mol with an excess of isocyanatopropyltrimethoxysilane, so as to result in an allophanate reaction after the polyurethane formation.

In DE102005041954A1, a polyurethane formed from a polyol and a diisocyanate (e.g. IPDI, isophorone diisocyanate) is admixed with isocyanatopropyltrimethoxysilane and heated until allophanate structures form.

EP2089444A1 claims allophanate-containing polyurethanes which, as well as an unsaturated functionality, also have silane-containing components.

The situation is similar in EP2089445A1; here, however, these polyurethanes additionally have to contain a dispersion-active component in order to make them water-compatible.

US20140097392A1 also discusses allophanate- and alkoxysilane-containing polymers, which in this case are blended with a dye.

J. Kozakiewicz et al. published, in *Progress in Organic Coatings* 72 (2011) 120-130, silane-containing blocking agents for polyisocyanates which have been introduced via an allophanate group.

There is obviously a need for further compounds bearing alkoxysilane groups, particularly for scratch-resistant applications. However, it is common to all the existing examples that they are always polymers and/or polyurethanes which both have high viscosities and are difficult to purify or to isolate.

The problem addressed by this invention was that of making available novel compounds bearing alkoxysilane groups and having scratch-resistant properties, which do not have the disadvantage of the prior art, but are especially easy to prepare, have low viscosities and can be purified with a low level of complexity.

It has been found that, surprisingly, monoallophanates consisting of an isocyanate-modified monourethane containing alkoxysilane groups have the desired properties.

The invention accordingly provides monoallophanates having the formula 1:

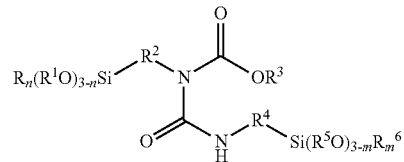

where R, $R^1$-$R^5$ are each independently identical or different hydrocarbyl radicals having 1-8 carbon atoms, which may be branched or cyclic, or else may be integrated together to form a cyclic system, and m and n are each independently 0-2.

Preferably, m and n are each 0.

$R^1$ and $R^5$ are each independently preferably methyl or ethyl.

$R^2$ and $R^4$ are preferably each independently methyl or propyl.

More preferably, $R^1$=$R^5$ and $R^2$=$R^4$.

Preference is given to compounds where m and n are each 0, $R^1$ and $R^5$ are each methyl or ethyl, and $R^2$ and $R^4$ are methyl or propyl.

Very particular preference is given to the compound where m and n are each 0, $R^1$=$R^5$=methyl and $R^2$=$R^4$=propyl.

The invention also provides a process for preparing the monoallophanates according to the invention by a reaction of A) an isocyanate containing alkoxysilane groups
   with
B) a monourethane containing alkoxysilane groups,
   at temperatures in the range from 20 to 220° C.

Alkoxysilane-containing isocyanates A) have the formula 2:

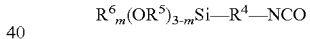

where $R^6$, $R^5$ and $R^4$ are each independently identical or different hydrocarbyl radicals having 1-8 carbon atoms, which may be branched or cyclic, or else may be integrated together to form a cyclic system, and m is 0-2.

Preferably, m=0.

$R^4$ is preferably methyl or propyl.

$R^5$ is preferably methyl or ethyl.

Preference is given to compounds where m is 0 and $R^4$ is methyl or propyl, and $R^5$ is methyl or ethyl.

Particular preference is given to isocyanatopropyltrimethoxysilane.

Alkoxysilane-containing monourethanes B) have the formula 3:

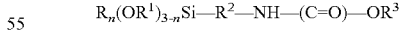

where R, $R^1$, $R^2$ and $R^3$ are each independently identical or different hydrocarbyl radicals having 1-8 carbon atoms, which may be branched or cyclic, or else may be integrated together to form a cyclic system, and n is 0-2.

Preferably, n=0.

$R^1$ is preferably methyl or ethyl.

$R^2$ is preferably methyl or propyl.

Preferably, $R^3$=$R^1$.

Preference is given to compounds where n is 0 and $R^2$ is methyl or propyl, and $R^1$ is methyl or ethyl and $R^3$=$R^1$.

Particular preference is given to N-trimethexysilylpropylmethyl carbamate.

The monoallophanates according to the invention are generally prepared solventlessly or using non-protic solvents, and the reaction may take place batchwise or continuously. The reaction is conducted in suitable equipment, for example stirred tanks, extruders, static mixers, kneading chambers. The reaction may be operated at room temperature, in other words at temperatures in the range from 20 to 22° C., though preferably higher temperatures are used, in the range from 80 to 220° C., more particularly in the range from 80 to 120° C. To accelerate the reaction, it is advantageously possible to use catalysts known in urethane chemistry, for example organometallic compounds such as tin or zinc compounds, salts, for example Zn(II) chloride, and/or bases. Suitable examples are carboxylates of Sn, Bi, Zn and other metals, for example dibutyltin dilaurate, tin octoate, bismuth neodecanoate, tert-amines, for example 1,4-diazabicyclo[2.2.2]octane (DABCO), triethylamine, amidines and guanidines, and quaternary ammonium salts, preferably tetraalkylammonium salts, and/or quaternary phosphonium salts.

Useful catalysts include metal acetylacetonates. Examples thereof are zinc acetylacetonate, lithium acetylacetonate, iron acetylacetonate and tin acetylacetonate, alone or in mixtures. Preference is given to using zinc acetylacetonate. Useful catalysts are also quaternary ammonium acetylacetonates or quaternary phosphonium acetylacetonates.

The reaction is conducted with exclusion of water. Preference is given to conducting the reaction solventlessly.

Also provided by the invention is the use of the monoallophanates according to the invention in paint compositions for metal, plastic, glass, wood, MDF (Middle Density Fibreboard) or leather substrates or other heat-resistant substrates.

Also provided by the invention is the use of the monoallophanates according to the invention in adhesive compositions for bonds of metal, plastic, glass, wood, MDF or leather substrates or other heat-resistant substrates.

The present invention is more particularly illustrated by the following non-limiting examples from which further features, embodiments, aspects and advantages of the present invention may be discerned.

EXAMPLES

1)
Preparation of the monoallophanates according to the invention
a)
236 g (1 mol) of trimethoxysilylpropylmethyl carbamate (Evonik Industries AG) and 205 g of isocyanatopropyltrimethoxysilane (Evonik Industries AG) are mixed with one another and heated to 175° C. for 2 h. Thereafter, the starling materials are removed at 100° C. and 0.3 mbar by means of a short-path distillation. This leaves 183 g (41.5%) of a clean, water-clear liquid.

C13-NMR in CDCl$_3$ (ppm): 156.9 (1); 154.4 (1); 53.5 (1); 50.5 (10); 46.3 (1); 43.2 (1); 23.2 (1); 22.6 (1). 6.7 (1); 6.5 (1).

Viscosity is about 200 mPas and hence is very low.
b)
236 g (1 mol) of trimethoxysilylpropylmethyl carbamate (Evonik Industries AG), 205 g of isocyanatopropyltrimethoxysilane (Evonik Industries AG) and 0.4 g of tin(II) chloride are mixed with one another and heated to 150° C. for 1 h. Thereafter, the starting materials are removed at 90° C. and 0.3 mbar by means of a short-path distillation. This leaves 339 g (76.9%) of a clean, water-clear liquid. (for NMR see above)
c)
236 g (1 mol) of trimethoxysilylpropylmethyl carbamate (Evonik Industries AG), 205 g of isocyanatopropyltrimethoxysilane (Evonik Industries AG) and 1 g of iron(III) acetylacetonate are mixed with one another and heated to 90° C. for 3 h. Thereafter, the starling materials are removed at 90° C. and 0.3 mbar by means of a short-path distillation. This leaves 184 g (41.5%) of a clean, water-clear liquid. (for NMR see above)
2)
Paint Formulation:
44.5 g of Setalux 1760 (OH-functional acrylate, Nuplex industries) and 30 g of inventive product a) are mixed with 25 g of butyl acetate/xylene (1:1), and 0.5 g of catalyst (VESTANAT EP-CAT 11, Evonik Industries AG) is added. This mixture is coated onto a steel sheet with a 120 μm spiral coating bar and baked at 140° C. for 22 min. The coating (layer thickness 30 μm) has a pendulum hardness of 176 s and a chemical resistance of >150 MEK twin strokes. It is thus fully cured.

Scratch Resistance:
The starting gloss is 86 scale divisions (SD) (20°) After the brush test, the gloss has dropped to 84 SD. The Crockmeter test leads to a gloss of 83 SD. The loss of gloss is thus 2 or 3 SD and hence the scratch resistance is excellent.

Evaluation: loss of gloss resulting from scratches 0-9 SD excellent, 10-20 very good, 21-34 good, 35-44 average, >45 poor By comparison, commercial 2-pack PUR paints based on Setalux 1760 have a loss of gloss of about 30 SD.

Brush Test (Wet):
Instrument: U 1 Serial no. 003, manufacturer: BASF L+F, built: 1993
The paint surface is damaged with a screen fabric (nylon screen fabric no, 11, mesh size 25 μm) under a weight (2 kg). The screen fabric and the paint surface are wetted copiously with a detergent solution (0.25% Persil solution in water). The test panel is moved in backward and forward strokes under the screen fabric with the aid of a motor drive. The gloss is measured before and after the test.

Crockmeter Test (Dry)
Instrument: U 1 Serial no. 003, manufacturer: BASF L+F, built: 1993
The paint surface is damaged with a fabric (3M 281Q WetODry Polishing Paper) under a weight (920 g). The test panel is moved in backward and forward strokes under the fabric with the aid of a motor drive.

The invention claimed is:
1. A monoallophanate having the formula (1):

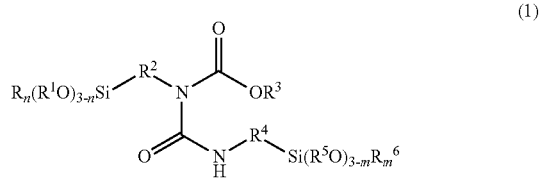

wherein
R, R$^1$-R$^6$ are each independently identical or different hydrocarbyl radicals having 1-8 carbon atoms, which may be branched or cyclic, or else may be integrated together to form a cyclic system, and m and n are each 0.

2. The monoallophanate according to claim 1, wherein $R^1$ and $R^5$ are each independently methyl or ethyl.

3. The monoallophanate according to claim 1, wherein $R^2$ and $R^4$ are each independently methyl or propyl.

4. The monoallophanate according to claim 1, wherein $R^1=R^5$ and $R^2=R^4$.

5. The monoallophanate according to claim 1, wherein $R^1$ and $R^5$ are each methyl or ethyl, and
$R^2$ and $R^4$ are each methyl or propyl.

6. The monoallophanate according to claim 1, wherein $R^1=R^5=$methyl, and
$R^2=R^4=$propyl.

7. A process for preparing the monoallophanate according to claim 1, the process comprising:
reacting
A) an isocyanate comprising at least one alkoxysilane group
with
B) a monourethane comprising at least one alkoxysilane group,
at temperatures in the range from 20 to 220° C.

8. The process for preparing the monoallophanate according to claim 7,
wherein the monourethane of B) is represented by formula (3):

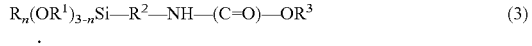  (3)

wherein
R, $R^1$, $R^2$ and $R^3$ are each independently identical or different hydrocarbyl radicals having 1-8 carbon atoms, which may be branched or cyclic, or else may be integrated together to form a cyclic system.

9. The process for preparing the monoallophanate according to claim 8, wherein
$R^2$ is methyl or propyl, and
$R^1$ is methyl or ethyl and $R^3=R^1$.

10. The process for preparing the monoallophanate according to claim 8, wherein
the monourethane of B) is N-trimethoxysilylpropylmethyl carbamate.

11. The process for preparing the monoallophanate according to claim 7,
wherein the isocyanate of A) is represented by formula (2):

  (2)

wherein
$R^6$, $R^5$ and $R^4$ are each independently identical or different hydrocarbyl radicals having 1-8 carbon atoms, which may be branched or cyclic, or else may be integrated together to form a cyclic system.

12. The process for preparing the monoallophanate according to claim 11, wherein
$R^4$ is methyl or propyl, and
$R^5$ is methyl or ethyl.

13. The process for preparing the monoallophanate according to claim 11, wherein
the isocyanate of A) is isocyanatopropyltrimethoxysilane.

14. A paint composition, which comprises the monoallophanate according to claim 1.

15. An adhesive composition, which comprises the monoallophanate according to claim 1.

* * * * *